US007923255B2

(12) United States Patent
Ono

(10) Patent No.: US 7,923,255 B2
(45) Date of Patent: Apr. 12, 2011

(54) METHOD OF DETECTING PLATELET THROMBOSIS OR ORGAN FAILURE

(75) Inventor: Tomoko Ono, Toyko (JP)

(73) Assignee: Mitsubishi Chemical Medience Corp., Tokyo (JP)

( * ) Notice: Subject to any disclaimer, the term of this patent is extended or adjusted under 35 U.S.C. 154(b) by 537 days.

(21) Appl. No.: 11/718,853

(22) PCT Filed: Nov. 8, 2005

(86) PCT No.: PCT/JP2005/020451
§ 371 (c)(1), (2), (4) Date: May 8, 2007

(87) PCT Pub. No.: WO2006/049300
PCT Pub. Date: May 11, 2006

(65) Prior Publication Data

US 2008/0096221 A1 Apr. 24, 2008

(30) Foreign Application Priority Data

Nov. 8, 2004 (JP) ................................ 2004-323770

(51) Int. Cl.
*G01N 33/86* (2006.01)
*G01N 33/53* (2006.01)

(52) U.S. Cl. .............. 436/69; 435/4; 435/7.1; 435/7.92; 435/13; 435/218; 436/517; 436/177; 436/811

(58) Field of Classification Search ............... 435/4, 7.1, 435/7.92, 13, 218; 436/506, 518, 548, 16, 436/69, 177, 811, 517
See application file for complete search history.

(56) References Cited

U.S. PATENT DOCUMENTS

| | | | | |
|---|---|---|---|---|
| 7,575,872 | B2 | 8/2009 | Soejima et al. | |
| 2004/0214346 | A1 * | 10/2004 | Scheiflinger et al. | 436/518 |
| 2008/0096221 | A1 * | 4/2008 | Ono | 435/7.1 |
| 2009/0220990 | A1 * | 9/2009 | Igami et al. | 435/7.4 |

FOREIGN PATENT DOCUMENTS

| | | | |
|---|---|---|---|
| EP | 1568782 | | 6/2005 |
| EP | 1 544 293 | * | 6/2006 |
| JP | 2004-261067 | | 9/2004 |
| WO | 96/40224 | | 12/1996 |

(Continued)

OTHER PUBLICATIONS

Konetschny et al. Development of a Highly Sensitive and Specific Enzyme-linked Immunosorbent Assay for the Detection of ADAMTS-13 in Human Plasma, Blood 102 (11) Abstract #4062 (Nov. 16, 2003).*

(Continued)

*Primary Examiner* — Gailene R Gabel
(74) *Attorney, Agent, or Firm* — Heslin Rothenberg Farley & Mesiti P.C.

(57) ABSTRACT

A method of detecting platelet thrombosis or organ failure in a patient suffering from disseminated intravascular coagulation (DIC) or systemic inflammatory response syndrome (SIRS), comprising analyzing a von Willebrand factor-cleaving protease and/or a cleaving factor thereof, is disclosed. A kit for detecting platelet thrombosis or organ failure in a patient suffering from DIC or SIRS, comprising an antibody or a fragment thereof which specifically binds to a von Willebrand factor-cleaving protease, and/or an antibody or a fragment thereof which specifically binds to a cleaving factor of the von Willebrand factor-cleaving protease, is disclosed.

10 Claims, 3 Drawing Sheets

FOREIGN PATENT DOCUMENTS

WO 2004/095027 11/2004

OTHER PUBLICATIONS

Crawley et al., Proteolytic inactivation of ADAMTS 13 by thrombin and plasmin (Hemostasis, Thrombosis, and Vascular Biology, Blood 105 (3): 1085-1093).*
Bone, Roger C., "Sir Isaac Newton, sepsis, SIRS, and CARS", 1996, vol. 24, No. 7., pp. 1125-1128.
Davies, M.G. et al, "Systemic Inflammatory Response Syndrome", British Journal of Surgery, 1997, vol. 84, pp. 920-935.
Gando, Satoshi et al., "Disseminated Intravascular Coagulation is a Frequent Complication of Systematic Inflammatory Response Syndrome", Thrombosis and Haemostasis, 1996, pp. 224/228.
Gando, Satoshi et al., "Soluble Thrombomodulin Increases in Patients with Disseminated Intravascular Coagulation and in those with Multiple Organ Dysfunction Syndrome After Trauma; Role of NEutrophil Elastase", The Journal of Trauma, 1995, pp. 660-664.
Rothenburger, Markus et al., "Leukocyte Activation and Phagocytotic Activity in Cardiac Surgery and Infection" Cardiovascular Surgery, 2002, vol. 10, No. 5, pp. 470-475.
Saito, Takatoshi et al., "Microscopic Polyangiitis Associated with Marked Systematic Bleeding Tendency Caused by Disseminated Intravascular Coagulation", Internal Medicine, Sep. 2003, vol. 42, No. 9, pp. 850-855.
Crawley, James T.B. et al., "Proteolytic Inactivation of ADAMTS13 by Thrombin and Plasmin", Blood, Feb. 1, 2005, vol. 105, No. 3, pp. 1085-1093.
Moore et al. "Decreased von Willebrand Factor Protease Activity Associated with Thrombocytopenic Disorders". Blood, vol. 98, No. 6, 1842-1846 (2001).
Rick et al., "Clinical Usefulness of a Functional Assay for the von Willebrand Factor Cleaving Protease (ADAMTS 13) and Its Inhibitor in a Patient with Thrombotic Thrombocytopenic Purpura", American Journal of Hematology 75 (2):96-100 (2004).
Ono et al., "Severe secondary deficiency of von Willebrand factor-cleaving protease (ADAMTS13) in patients with sepsis-induced disseminated intravascular coagulation: its correlation with development of renal failure", Blood, Jan. 15, 2006, vol. 107(2), 528-533.
Konetschny et al., "Development of a highly sensitive and specific enzyme-linked immunosorbent assay for the detection of ADAMTS-13 in human plasma", Blood, American Society of Hematology, US, vol. 102(11), Nov. 16, 2004, p. 89b, (Abstract).
Obert et al., "Estimation of the von Willebrand Factor-cleaving Protease in Plasma Using Monoclonal Antibodies to vWF", Thrombosis and Haemostasis, Stuttgart, DE., vol. 82(5), Nov. 1, 1999, p. 1382-1385.
Supplementary European Search Report dated Oct. 14, 2008.
Written Opinion of the International Search Report corresponding to PCT/JP2005/020451, (Apr. 2005).

* cited by examiner

194kDa

116kDa

95kDa

51kDa

METHOD OF DETECTING PLATELET THROMBOSIS OR ORGAN FAILURE

CROSS REFERENCE TO RELATED APPLICATIONS

This application is a 35 U.S.C. §371 U.S. national stage filing from PCT Application Ser. No. PCT/JP2005/020451, having an international filing date of Nov. 8, 2005, published in English on May 11, 2006 under Publication No. W02006/049300, which claims priority from Application Ser. No. 2004-323770, filed Nov. 8, 2004, which are hereby incorporated by reference in their entirety.

TECHNICAL FIELD

The present invention relates to a method of detecting platelet thrombosis or organ failure, particularly in a patient suffering from disseminated intravascular coagulation (DIC) or systemic inflammatory response syndrome (SIRS). According to the present invention, a von Willebrand factor (VWF)-cleaving protease and/or a cleaving factor thereof contained in a biological sample such as blood collected from a subject, particularly a patient suffering from DIC or SIRS, may be analyzed to detect platelet thrombosis or organ failure. The detection of platelet thrombosis or organ failure includes, for example, a detection or a prediction of platelet thrombus formation, a prediction of the development of thrombosis or organ failure (i.e., an evaluation of a risk of the development), a judgment of a presence or absence of thrombosis or organ failure, a prognosis of thrombosis or organ failure, a monitoring, and a decision about a treatment.

BACKGROUND ART

In DIC, microthrombi are formed in microvasculature, in the presence of a severe underlying disease. The microthrombi damage the microcirculation and cause an organ dysfunction or a bleeding tendency. The symptoms of DIC are associated with SIRS. The following three failures or reactions are observed in DIC:

(1) The microthrombus formation causes a microcirculatory failure, and a variety of organs fall into dysfunction due to ischemia.

(2) The microthrombus formation promotes a consumption coagulopathy, that is, increasing of tissue factor production on the surface of endothelial cells leads to activation of extrinsic coagulation pathway. Further, coagulation factors and platelets are consumed, and a bleeding tendency occurs.

(3) Hyperfibrinolysis, that is, the fibrinolytic system activated according to the activation of coagulation, generates plasmin, which degrades fibrin. When the $\alpha_2$-plasmin inhibitor ($\alpha_2$PI), which inhibits plasmin, is consumed and decreased to less than 60% of the normal level, fibrin is degraded by the plasmin and a bleeding tendency occurs.

In sepsis-induced DIC, cytokines generated from monocytes (macrophage), such as tumor necrosis factors (TNF-$\alpha$) or interleukins (IL-1$\beta$), activate neutrophils. Active oxygen and neutrophil elastase produced from neutrophils damage vascular endothelial cells, which leads to hyperpermeability of the vascular endothelium and vasospasm. As a result, the microcirculation is damaged. Further, it is considered that monocytes per se and vascular endothelial cells are activated, and tissue factors are produced on the endothelial cell surfaces to form microthrombi. This microthrombus formation aggravates microcirculatory failure and causes multiple organ failure (MOF). According to a recent popular SIRS concept, this MOF is considered to be caused by a systemic inflammatory reaction. In adult respiratory distress syndrome (ARDS), platelets concentrate in the pulmonary circulation, and an occlusion of the pulmonary artery occurs. In SIRS, neither a reaction to a specific antigen nor an increased cytokine causes the inflammatory reaction. SIRS is a syndrome in which the inflammatory reaction is activated, without such a specific target, by nonspecifically reacting with an invasion to a living body and an uncontrollable cytokine production causes severe MOF (non-patent references 1 and 2).

SIRS is classified into noninfectious SIRS and sepsis. Noninfectious SIRS is caused by shock, injury, burn, or acute pancreatitis, and sepsis is caused by bacteremia by various pathogenic bacteria, or other severe infectious diseases. Sepsis is a biological immune response per se against an invasion of a pathogen, an injury of a tissue, or anoxia, and a nonspecific and systemic acute inflammatory reaction caused by various endogenous mediators, independently of the type of invasion. Organ failure accompanied by SIRS is sometimes caused by an inflammation or ischemia of a tissue, at the early stage. However, in the multiple organ dysfunction syndrome (MODS) caused by prolonged SIRS, biological overreactions via various mediators are involved in an aggravation of the conditions, and thus it is difficult to predict the prognosis of SIRS.

In SIRS, inflammatory cytokines such as TNF-$\alpha$, IL-1 (interleukin-1), or IL-6 (interleukin-6) are increased in blood. In particular, TNF-$\alpha$ is considered to be a cytokine which activates neutrophils and promotes a coagulation reaction in SIRS. When the activation of neutrophils exceeds the cytoprotective functions of vascular endothelial cells, vascular endothelial cells are damaged by proteases such as neutrophil elastase or cathepsin G, and thus, the microcirculation is damaged and microthrombi are formed. The activated neutrophils accumulate not only at the irritated area, but also at distant organs such as the lungs or the liver (leukocytes easily adhere thereto due to a low perfusion pressure). It is considered that microthrombi formation causes a stasis and ischemia of tissues and, as a result, MOF is caused. Further, neutrophils infiltrate into extravasculature to damage organs. When the microthrombus formation continues, coagulation factors and platelets are consumed. When the state of SIRS continues for 3 days or more, the patient is associated strongly with DIC. As described above, DIC is closely related to SIRS.

Neutrophil elastase is a neutral protease having a molecular weight of approximately 30,000 and located in azurophile granules. Under physiological conditions, neutrophil elastase digests and degrades phagocytosed bacteria or foreign bodies on the inside of neutrophils, and digests elastin, collagen (type III, type IV), fibronectin, immunoglobulin, or coagulation factor XIII on the outside of neutrophils, to regulate the biosynthesis of tissues. Under disease conditions, neutrophil elastase inactivates biological components, such as elastic fibers, proteoglycans, collagen fibers, antithrombin III, or $\alpha_2$-plasmin inhibitor. When neutrophil elastase acts on a heparin binding site of antithrombin III to inactivate antithrombin III, DIC is caused. Neutrophil elastase is inactivated by $\alpha_1$-antitrypsin ($\alpha_1$-AT) which is an inhibitor of elastase for 3 msec. in blood. However, in an inflammatory tissue, it is considered that $\alpha_1$-AT is oxidized by active oxygen, myeloperoxidase, and/or lactoferrin released from neutrophils, and thus, neutrophil elastase is not inactivated and damage is caused to the tissue. Since neutrophil elastase shows a low substrate specificity, when neutrophil elastase is overreleased or an inhibitor such as $\alpha_1$-AT is decreased, there is a possibility that neutrophil elastase degrades the biological components and damages its own tissues. Severely damaged vascular endothelial cells are injured, and platelets adhere and aggregate to the injured area to form thrombi.

This adhesion of platelets requires human VWF in plasma, and triggers a series of platelet activation including a platelet aggregation and a release of intracellular granules, and then formed thrombi lead to hemostasis. In general, the VWF is secreted from vascular endothelium to blood as a macromolecule having a molecular weight of more than 20,000 kDa, and is cleaved by a metalloprotease, VWF-cleaving protease, into multimers of 500 to 20,000 kDa, which circulate through the blood. In some disease states (i.e., when a high shear stress is caused by occlusion or the like), the protein structures of the VWF change to an extended structure. The extended VWF is resistant to the VWF-cleaving protease. It is considered that when "unusually large" VWF molecules are overproduced in the blood and bind to platelets then, as a result, the platelet aggregation in blood vessels is promoted to form thrombi in microcirculation. Such thrombus formation involved in platelets is essential for physiological hemostatic mechanisms. However, activation of coagulation factors (such as factor VII or factor II) leads to the thrombus formation by fibrin formation and platelet fusion.

DISCLOSURE OF THE INVENTION

Problems to be Solved by the Invention

As described above, with respect to the formation of thrombi involved in platelets and thrombi involved in fibrin, no factor which can explain the mechanisms of the formation has been reported. However, it is considered that a bad prognosis observed in patients with DIC or SIRS can be alleviated by clarifying mechanisms of the formation of microthrombi formed from fibrin and platelets in microvasculature. Further, there is a possibility that the development of organ failure can be prevented by an appropriate treatment at an early stage. The present inventor has conducted intensive studies, and found that the VWF-cleaving protease is degraded by elastase, plasmin, or thrombin, that the types of degradation caused thereby are different from each other, and that concentrations of the VWF-cleaving protease in plasma collected from patients with DIC or SIRS in which an elastase level is high are significantly decreased, in comparison with healthy persons, to complete the present invention.

An object of the present invention is to provide a method of detecting platelet thrombosis or organ failure in a subject, particularly a patient with DIC or SIRS, and a kit for detecting the same.

Means for Solving the Problems

The object can be solved by the present invention, that is, a method of detecting platelet thrombosis or organ failure in a patient suffering from disseminated intravascular coagulation or systemic inflammatory response syndrome, comprising analyzing a von Willebrand factor-cleaving protease and/or a cleaving factor thereof.

According to a preferred embodiment, the cleaving factor is a protease selected from the group consisting of elastase, plasmin, and thrombin, more preferably elastase.

According to another preferred embodiment, the von Willebrand factor-cleaving protease is immunologically analyzed.

According to still another preferred embodiment, the analysis is carried out after a pharmaceutical composition is administered to the patient, the pharmaceutical composition containing as an active ingredient an antagonist, an inhibitor, an agonist, or a modulator of the von Willebrand factor-cleaving protease activity.

According to still another preferred embodiment, the analysis is carried out after a pharmaceutical composition is administered to the patient, the pharmaceutical composition containing as an active ingredient an antagonist, an inhibitor, an agonist, or a modulator of an activity of a protease selected from the group consisting of elastase, plasmin, and thrombin.

The present invention relates to a kit for detecting platelet thrombosis or organ failure in a patient suffering from disseminated intravascular coagulation or systemic inflammatory response syndrome, comprising an antibody or a fragment thereof which specifically binds to a von Willebrand factor-cleaving protease, and/or an antibody or a fragment thereof which specifically binds to a cleaving factor of the von Willebrand factor-cleaving protease.

A preferred embodiment of the kit of the present invention further comprises an antibody or a fragment thereof which specifically binds to a von Willebrand factor-cleaving protease cleaved by a protease selected from the group consisting of elastase, plasmin, and thrombin.

The term "analysis" as used herein includes a detection to determine a presence or absence of a substance (for example, VWF-cleaving protease) to be analyzed, and a measurement to quantitatively or semi-quantitatively determine an amount of a substance to be analyzed.

EFFECTS OF THE INVENTION

The present invention enables a detection of platelet thrombosis or organ failure in a subject, such as a patient suffering from DIC or SIRS, particularly DIC or SIRS associated with an underlying disease such as acute myeloid leukemia, metastatic lung cancer, and/or urinary tract infection in which a concentration of elastase is high, and is clinically valuable. According to the present invention, thrombosis or the degree of organ failure can be detected conveniently, rapidly, and specifically.

BRIEF DESCRIPTION OF THE DRAWINGS

FIG. 1 is a photograph showing the result of electrophoresis of a recombinant VWF-cleaving protease antigen treated with elastase.

BEST MODE FOR CARRYING OUT THE INVENTION

Figure 2:
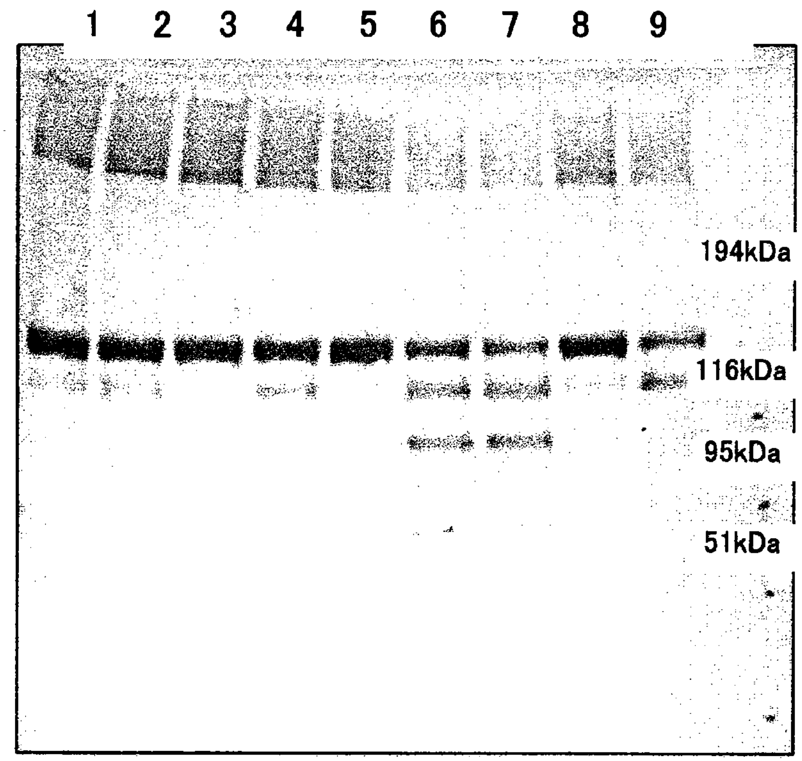
FIG. 2 is a photograph showing the result of electrophoresis of a recombinant VWF-cleaving protease antigen treated with plasmin or thrombin.

[1] Detection Method of the Present Invention

In the method of the present invention, thrombosis or organ failure can be detected or diagnosed by measuring an amount (or concentration) of the VWF-cleaving protease and/or a cleaving factor thereof, or an enzyme activity thereof, and comparing the obtained value with that of a healthy person. The detection of thrombosis or organ failure, as used herein, includes, for example, a detection or a prediction of the degree of platelet thrombus formation, a prediction of the development of thrombosis or organ failure (i.e., an evaluation of a risk of the development), a judgment of a presence or absence of thrombosis or organ failure, a prognosis of thrombosis or organ failure, a monitoring, and a decision about a treatment.

In the method of the present invention, either an amount (or concentration) of the VWF-cleaving protease or a cleaving factor thereof, or an enzyme activity thereof can be analyzed, and it is preferable to analyze the amount (or concentration). Hereinafter the present invention will be mainly explained on the basis of the preferred embodiment in which the amount (or concentration) of the VWF-cleaving protease or a cleaving factor thereof is analyzed. The following descriptions may be applied to an embodiment in which the enzyme activity is analyzed.

The term "von Willebrand factor-cleaving protease (VWF-cleaving protease)" as used herein means a metalloprotease, sometimes referred to as ADAMTS13, which specifically cleaves the von Willebrand factor (VWF) at the bond between tyrosine (842) and methionine (843) contained in an A2 domain thereof.

In the method of the present invention, a decreased concentration of the VWF-cleaving protease may be used as an index, in comparison with that of healthy people. As shown in Example 3 described below, a concentration of the VWF-cleaving protease contained in each body fluid sample collected from patients suffering from DIC or SIRS in which a concentration of elastase is high (for example, 100 ng/mL or more) is significantly decreased (50% or more), in comparison with healthy people. Therefore, in the method of the present invention, when a measured concentration of the VWF-cleaving protease in a subject to be judged is lower than a normal range of healthy people (for example, lower than a threshold), it can be judged that the degree of platelet thrombus formation is high, a risk of the development of thrombosis or organ failure is high, and the prognosis of thrombosis or organ failure is bad. In contrast, when a measured concentration of the VWF-cleaving protease in a subject to be judged is within a normal range of healthy people, it can be judged that the degree of platelet thrombus formation is low, a risk of the development of thrombosis or organ failure is low, and the prognosis of thrombosis or organ failure is good.

A subject to which the method of the present invention can be applied is not limited, so long as the subject is in need of a detection of the degree of platelet thrombus formation, or a prediction of the development or prognosis of thrombosis or organ failure (for example, renal damage or liver damage, preferably renal damage). As the subject, there may be mentioned, for example, a patient suffering from DIC or SIRS, preferably a patient suffering from DIC or SIRS in which a concentration of elastase is high, such as a patient suffering from DIC or SIRS associated with an underlying disease such as leukemia (such as acute myeloid leukemia), an infection (such as urinary tract infection), or a cancer (such as metastatic lung cancer).

In thrombosis, blood coagulates in a vessel, which is narrowed or completely blocked by thrombi which adhere on the wall of the vessel, and then the hampering of the blood flow damages a tissue or an organ. When a vessel is injured, platelets in blood accumulate at the wound and lead to hemostasis. Then, fibrin in blood aggregates thereon to form thrombi, which complete the hemostasis, and the vessel is repaired by a proliferation of vessel wall cells. Under normal conditions, these thrombi are lysed by the components which can act on the thrombi, and the blood flow returns. Thrombosis is a disease in which such a fibrinolytic system does not work properly, and thrombi inhibit or completely block the blood flow. It is considered that a fifth of people in their forties, a third of people in their fifties, a half of people in their sixties, and almost all of people in their seventies, suffer from thrombosis. As the main symptoms of thrombosis, there may be mentioned, for example, cerebral thrombosis, cerebral embolism, or transient ischemic attack in the brain; pulmonary thromboembolism in lungs; angina pectoris, myocardial infarction, or intra-atrial thrombosis in the heart; or mesenteric thrombosis or deep vein thrombosis (economy-class syndrome).

In the method of the present invention, the detection and/or the prediction can be carried out by collecting samples from a subject, such as a patient suffering from DIC or SIRS, and from a healthy person, measuring concentrations of the VWF-cleaving protease contained in the samples, and comparing the measured values. In general, it is preferable that samples collected from healthy people are used to determine a normal range of the VWF-cleaving protease concentration, or a threshold thereof for judgment in advance. When the normal range or the threshold for judgment is determined in advance, the detection and/or the prediction in a subject can be carried out by analyzing only the VWF-cleaving protease contained in the sample collected from the subject. The normal range or the threshold for judgment is considered to depend on various conditions, such as an underlying disease, sex, or age. However, those skilled in the art can easily determine the normal range or the threshold for judgment, by selecting an appropriate statistical population corresponding to the subject(s) and statistically processing data obtained from that population.

In the method of the present invention, a method of analyzing the VWF-cleaving protease is not limited, so long as an amount of the VWF-cleaving protease may be quantitatively or semi-quantitatively determined, or a presence or absence of the VWF-cleaving protease may be judged, by the analyzing method. As the analyzing method, there may be mentioned, for example, an immunological method using an anti-VWF-cleaving-protease antibody or a fragment thereof (such as an enzyme-linked immunosorbent assay, a latex agglutination immunoassay, a chemoluminescence immunoassay, a fluorescent antibody method, a radioimmunoassay, immunoprecipitation, immunohistochemical staining, or Western blotting), a biochemical method (such as an enzymological method), or a molecular biological method for measuring an mRNA.

When an immunological method is used in analyzing the VWF-cleaving protease, an anti-VWF-cleaving-protease antibody or a fragment thereof may be prepared in accordance with a known method, such as a method described in WO 2004/029242. Each immunoassay may be carried out in accordance with, for example, WO 2004/029242.

As a method of measuring the VWF-cleaving protease, an immunological method is preferable from the viewpoint of sensitivity and convenience. The immunological method means a method of analyzing the VWF-cleaving protease by an ELISA method, a latex method, immunochromatograpy, or the like, using an antibody against the VWF-cleaving protease. As the immunological method, there may be mentioned, for example, a competition method using a labeled VWF-cleaving protease, a sandwich method using a labeled antibody, a latex bead method in which an agglutination of beads coated with an antibody is observed, and a method using an antibody conjugated to a colored particle such as gold colloid. Any method using the antibody against the VWF-cleaving protease is included in preferred embodiments of the present invention. The antibody may be monoclonal or polyclonal. An antibody fragment, such as Fab, Fab', $F(ab')_2$, or Fv, may be used.

A preferred sample to be assayed by the method of the present invention is, for example, blood plasma. As samples other than the plasma, there may be mentioned, for example, various body fluids, such as cell or tissue fluids, lymph, a thymic fluid, a ascites fluid, an amniotic fluid, gastric juices, urine, pancreatic juices, spinal fluid, or saliva. The plasma is preferably citrated plasma or heparinized plasma.

In the method of the present invention, a cleaving factor of the VWF-cleaving protease may be analyzed, together with the analysis of the VWF-cleaving protease, or independently of the analysis of the VWF-cleaving protease. As the cleaving factor, for example, at least a protease selected from the group consisting of elastase, plasmin, and thrombin may be analyzed. As shown in Examples 1 and 2 described below, the present inventor found that the VWF-cleaving protease was cleaved by elastase, plasmin, or thrombin, and that the types of the cleavage were different. Therefore, a decrease in the VWF-cleaving protease is caused by the cleavage of the VWF-cleaving protease with elastase, plasmin, or thrombin.

In the method of the present invention, either the VWF-cleaving protease or a cleaving factor thereof may be analyzed to detect platelet thrombosis or organ failure. A more accurate detection or prediction may be carried out by analyzing both the VWF-cleaving protease and the cleaving factor (i.e., protease).

In the method of the present invention, a change in the concentration of the protease (i.e., cleaving factor) may be used as an index, in comparison with that of healthy people.

The protease concentration may be measured by various known methods described below. In blood, more than 90% of elastase exists in the form of a complex with α1-antitrypsin. This complex may be measured by an ELISA method using a monoclonal antibody. Thrombin generated in blood cannot be directly measured, because it is rapidly neutralized with various factors. However, an amount of thrombin may be approximately predicted as a complex with thrombin and antithrombin III (TAT). As in the case of thrombin, plasmin cannot be directly measured, because it rapidly disappears in blood. However, an amount of plasmin may be measured as a complex with plasmin and α2-antiplasmin (PIC). The complex TAT or PIC may be measured by, for example, an ELISA method or a latex agglutination method using a monoclonal or polyclonal antibody.

The method of present invention may be used to monitor the state of the patient (for example, an evaluation of the degree of platelet thrombus formation, or a prediction of the development or prognosis of thrombosis or organ failure) after administering a pharmaceutical composition to the patient. The pharmaceutical composition which may be used in the present invention is not limited, and there may be mentioned, for example, a pharmaceutical composition containing as an active ingredient an antagonist, an inhibitor, an agonist, or a modulator of an activity of the VWF-cleaving protease, or a pharmaceutical composition containing as an active ingredient an antagonist, an inhibitor, an agonist, or a modulator of an activity of a protease selected from the group consisting of elastase, plasmin, and thrombin.

With respect to the control of the formation of platelet thrombi and fibrin thrombi, the present inventor considers that elastase cleaves the VWF-cleaving protease to form platelet thrombi, and then fibrin adheres to form fibrin thrombi, and plasmin and/or thrombin secreted thereby cleave the VWF-cleaving protease, on the basis of the above-mentioned difference among the types of cleavage of the VWF-cleaving protease by each protease. For example, it is possible to accurately judge the conditions by understanding which protease affects a change in an amount of the VWF-cleaving protease.

For example, when an increased amount of elastase and a decreased amount of the VWF-cleaving protease are observed, it may be judged that this is the early stage in which platelet thrombi are formed. When an increased amount of plasmin or thrombin and a decreased amount of the VWF-cleaving protease are observed, it may be judged that this is the late stage in which fibrin thrombi have already been formed. A more appreciate treatment may be selected by understanding the disease conditions more accurately. The most preferable index is elastase, because it has the highest activity of cleaving the VWF-cleaving protease and is involved in the early stage.

[2] Detection Kit of the Present Invention

The kit of the present invention comprises at least an anti-VWF-cleaving-protease antibody or a fragment thereof, and/or an antibody or a fragment thereof which specifically binds to a cleaving factor of the VWF-cleaving protease. It is preferable that the kit of the present invention comprises two or more types of anti-VWF-cleaving-protease antibodies and/or two or more types of anti-cleaving-factor antibodies. The kit of the present invention further comprises an antibody or a fragment thereof which specifically binds to a VWF-cleaving protease cleaved by a protease selected from the group consisting of elastase, plasmin, and thrombin. The kit of the present invention may be used to carry out the method of the present invention.

The anti-VWF-cleaving-protease antibody or the anti-cleaving-factor antibody contained in the kit of the present invention may be a monoclonal antibody or a polyclonal antibody. When two or more types of anti-VWF-cleaving-protease antibodies or two or more types of anti-cleaving-factor antibodies are contained, one of the antibodies may be labeled as a second antibody, or a labeled anti-second-antibody antibody may be further added to the kit.

EXAMPLES

The present invention now will be further illustrated by, but is by no means limited to, the following Examples.

Example 1

Degradation of Recombinant VWF-Cleaving Protease Antigen by Elastase

Figure 1:
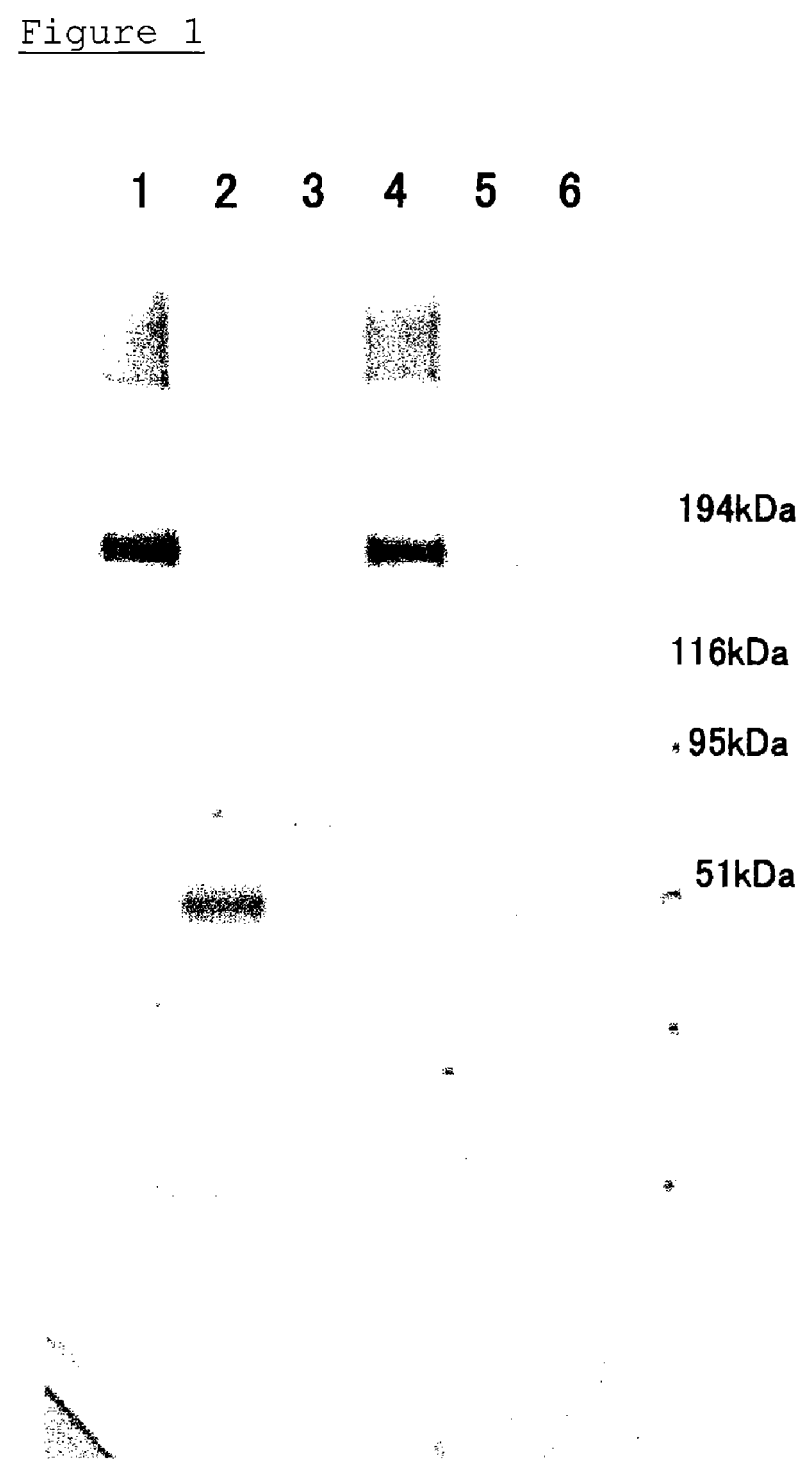

After 1.5 μg of a recombinant VWF-cleaving protease was dissolved in a Tris buffer/physiological saline solution, elastase was added to the solution to reach a final concentration of 20 nmol/L or 140 nmol/L. Each mixture was incubated at 37° C., and aliquots corresponding to 0.5 μg of the VWF-cleaving protease were collected therefrom after 15 minutes and 1 hour from the beginning of the incubation. The collected samples were subjected to an SDS electrophoresis (5-20% gel) under the non-reduced conditions, and transferred to a PVDF (polyvinylidene difluoride) membrane by Western blotting. The membrane was blocked with a commercially available blocking agent (Block Ace; Dainippon pharmaceutical) at room temperature for 30 minutes, and washed with a Tris buffer. The membrane was incubated in a 1 μg/mL anti-VWF-cleaving-protease monoclonal antibody (WH2-22-1A: epitope=a disintegrin region of VWF-cleaving protease)/Tris buffer (pH 7.4)/10% Block Ace solution at room temperature for 1 hour, and washed three times with a Tris buffer (pH 7.4)/0.05% NP-40 solution. The membrane was further incubated in a 1/2000-diluted anti-mouse-IgG antibody labeled with HRP (horseradish peroxidase) (Bio-Rad)/Tris buffer (pH 7.4)/10% Block Ace solution at room temperature for 1 hour, and washed three times with a Tris buffer (pH 7.4)/0.05% NP-40 solution. A coloring reaction was carried out using a TMB solution (Pierce). The result is shown in FIG. 1.

Reaction conditions in each lane shown in FIG. 1 are as follows:

Lane 1: Reaction without elastase

Lane 2: Reaction at 37° C. for 15 minutes with 20 nmol/L elastase

Lane 3: Reaction at 37° C. for 15 minutes with 140 nmol/L elastase

Lane 4: Reaction without elastase

Lane 5: Reaction at 37° C. for 1 hour with 20 nmol/L elastase

Lane 6: Reaction at 37° C. for 1 hour with 140 nmol/L elastase

In the reaction at 37° C. with 20 nmol/L elastase, most of the 160-kDa band of the VWF-cleaving protease was cleaved into the 50-kDa band after 15 minutes, and the 160-kDa band and most of the 50-kDa band disappeared after 1 hour, from the beginning of the reaction. In the reaction with 140 nmol/L elastase, all of the 160-kDa band was disappeared by the incubation for 15 minutes or more. This result suggested that the VWF-cleaving protease was degraded dependent on the time and on the concentration of elastase.

Example 2

Degradation of Recombinant VWF-Cleaving Protease Antigen by Plasmin or Thrombin After 1.5 μg of a recombinant VWF-cleaving protease was dissolved in a Tris buffer/physiological saline solution, a combination of plasminogen (final concentration=1 μmol/L) and tissue plasminogen activator (final concentration=0.2 nmol/L or 2 nmol/L), or thrombin (final concentration=20 mU or 200 mU) was added to the solution. Each mixture was incubated at 37° C., and aliquots corresponding to 0.5 μg of the VWF-cleaving protease were collected therefrom after 15 minutes and 1 hour from the beginning of the incubation. The collected samples were subjected to an SDS electrophoresis, and the Western blotting was carried out, as described in Example 1, to detect the bands of the VWF-cleaving protease. The result is shown in FIG. 2.

Reaction conditions in each lane shown in FIG. 2 are as follows:

Lane 1: Reaction at 37° C. for 15 minutes with 0.2 nmol/L tissue plasminogen activator (tPA)

Lane 2: Reaction at 37° C. for 15 minutes with 2 nmol/L tPA

Lane 3: Reaction at 37° C. for 15 minutes with 20 mmol/L thrombin

Lane 4: Reaction at 37° C. for 15 minutes with 200 mmol/L thrombin

Lane 5: Reaction without proteases

Lane 6: Reaction at 37° C. for 1 hour with 0.2 nmol/L tissue plasminogen activator (tPA)

Lane 7: Reaction at 37° C. for 1 hour with 2 nmol/L tPA

Lane 8: Reaction at 37° C. for 1 hour with 20 mmol/L thrombin

Lane 9: Reaction at 37° C. for 1 hour with 200 mmol/L thrombin

In either case of plasmin or thrombin, very little cleaving of the 160-kDa band occurred at 37° C. for 15 minutes. In the reaction at 37° C. with plasmin for 1 hour, the 130-kDa and 100-kDa bands, which were considered to be degradation products of the VWF-cleaving protease, appeared in addition to the 160-kDa band, regardless of the concentrations of plasmin added. In the reaction with thrombin for 1 hour, the 130-kDa band appeared when 200 mU of thrombin was added. This result indicated that plasmin and thrombin cleaved the VWF-cleaving protease at the same site, but at a different cleaving time.

Example 3

Correlation of VWF-Protease with Elastase

In this Example, plasma samples collected from healthy people, patients with DIC, and patients with SIRS were used to measure the amounts of the VWF-cleaving protease antigen and elastase contained therein. An amount of the VWF-cleaving protease antigen was measured using a commercially available kit (VWF-cleaving protease ELISA kit; Mitsubishi Kagaku Tatron). An amount of elastase was determined by measuring an amount of elastase/α1-antitrypsin using a commercially available kit (PMN Elastase/α1-PI Complex ELISA Kit; CALBIOCHEM).

Figure 3:
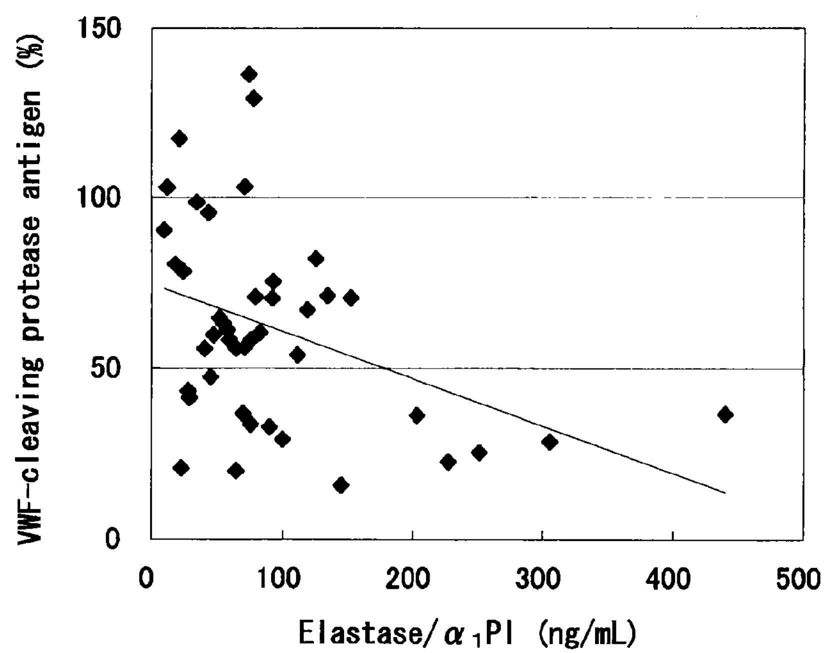
FIG. 3 is a graph showing the correlation between the VWF-cleaving protease and elastase.
Figure 4:
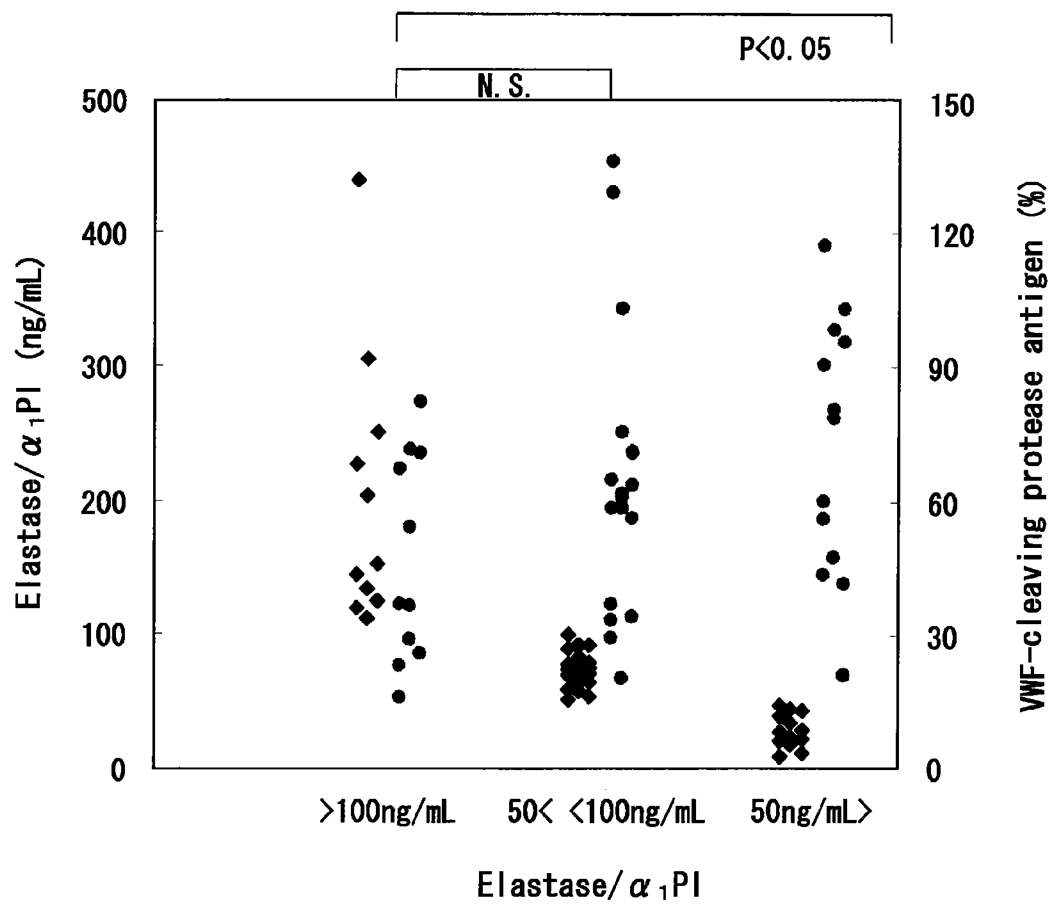
FIG. 4 is a graph showing the distribution of VWF-cleaving protease antigen levels in patient groups divided according to elastase levels.

The result is shown in FIGS. 3 and 4. In FIG. 3, the X axis indicates amounts of elastase/α1-antitrypsin (unit=ng/mL), and the Y axis indicates amounts of the VWF-cleaving protease antigen (unit=%). In FIG. 4, the abbreviation N.S. means that no significant difference existed therebetween.

There was a negative correlation between the amount of elastase/α1-antitrypsin and the amount of the VWF-cleaving protease antigen ($y=-0.1382x+74.643$; $R2=0.1549$). This result indicated that an amount of the VWF-cleaving protease antigen was lowered, due to the degradation of the VWF-cleaving protease antigen by elastase, in a patient with an increased elastase/α1-antitrypsin level, i.e., a patient in the state of MOF in which the tissue damage progresses. Further, the amount of the VWF-cleaving protease antigen in patients with an elastase level of 100 ng/mL or more was 46.4±23.2% (Mean ±SD), whereas that in patients with an elastase level of 50 ng/mL or less was 71.7±29.0%. It was found from this result that an amount of the VWF-cleaving protease antigen is significantly decreased in the patients with an elastase level of 100 ng/mL or more ($P<0.05$).

INDUSTRIAL APPLICABILITY

Cytokines such as TNF-α activate neutrophil and promote coagulation reaction, and proteases such as neutrophil elastase or cathepsin G damage vascular endothelial cells. According to the findings clarified by the present invention, under such conditions, elastase released into the blood, to repair the damaged tissue, actively cleaves the VWF-cleaving protease, so as to promote the formation of platelet thrombi. Further, it is suggested that when the coagulation reaction is promoted, fibrin aggregates on the platelet thrombi, and the plasmin system begins to work, plasmin cleaves the VWF-cleaving protease (after the above cleavage by elastase) and leads to the formation of microthrombi formed from fibrin and platelets in microvasculature, to develop DIC or SIRS. These findings are considered to be the first suggestion that the control of the VWF-cleaving protease by serine proteases is involved in the formation of platelet thrombi and fibrin thrombi. There remain various thromboses in which the mechanism cannot be explained on the basis of only degradation products of fibrin thrombi. There is a possibility that the present invention may clarify the mechanism of such thrombosis.

The present invention may be applied to the use for detecting platelet thrombosis or organ failure in a subject, such as patients with DIC or SIRS.

Patients suffering from DIC often develop conditions showing a bad prognosis, such as malignant diseases or severe diseases, and complicate the symptoms. In DIC, in the presence of various underlying diseases, the coagulation system is activated or regulatory factors for coagulation are decreased, and as a result, many microthrombi formed in microvasculature cause intravascular occlusion. Further, in DIC, consumptive hemostasis disorder caused by consuming platelets and coagulation and fibrinolysis factors is developed in addition to the thrombus formation, and a severe bleeding tendency and/or organ failure are observed. Therefore, it is very important to detect the microthrombus formation at the early stage to carry out an early treatment.

A predictive diagnosis of organ failure at the early stage in SIRS is useful as described below. A survival rate of cases with the development of MOF is not high, and there are cases in which the symptoms are not alleviated even when subjected to highly intensive care. Therefore, it is very important to detect a warning sign showing the transfer to organ failure as early as possible, to prevent a developing of an organ failure. That is, it is necessary to accurately judge the condition and/or the severity at the stage of SIRS, to take the proper treatment measures.

Although the present invention has been described with reference to specific embodiments, various changes and modifications obvious to those skilled in the art are possible without departing from the scope of the appended claims.

The invention claimed is:

1. A method of predicting the amount of a von Willebrand factor-cleaving protease in a patient suffering from disseminated intravascular coagulation or systemic inflammatory response syndrome, said method comprising:

collecting a sample of blood or plasma from the patient; and analyzing the blood or plasma sample for a significant increase in the amount of elastase, wherein the significant increase in the amount of said elastase is indicative of a significant decrease in the amount of said von Willebrand factor-cleaving protease.

2. The method according to claim 1, further comprising:

analyzing the sample for the amount of said von Willebrand factor-cleaving protease; and confirming that the prediction is correct by determining a decreased amount of the von Willebrand factor-cleaving protease.

3. The method according to claim 1, further comprising:

analyzing the sample for said von Willebrand factor-cleaving protease; and diagnosing the patient with platelet thrombosis, wherein the significant increase in said elastase and the significant decrease in said von Willebrand factor-cleaving protease are indicative of platelet thrombosis.

4. The method according to claim 1, further comprising:

analyzing the sample for said von Willebrand factor-cleaving protease; and diagnosing the patient with organ failure, wherein the significant increase in said elastase and the significant decrease in said von Willebrand factor-cleaving protease are indicative of organ failure.

5. The method according to claim 1, further comprising:

analyzing the sample for said von Willebrand factor-cleaving protease; and determining an appropriate treatment option, wherein the significant increase in said elastase and the significant decrease in said von Willebrand factor-cleaving protease are indicative of using an inhibitor of elastase.

6. A method of predicting the amount of elastase in a patient suffering from disseminated intravascular coagulation or systemic inflammatory response syndrome, said method comprising:

collecting a sample of blood or plasma from the patient; and analyzing the sample for a significant decrease in the amount of von Willebrand factor-cleaving protease, wherein the significant decrease in the amount of said von Willebrand factor-cleaving protease is indicative of a significant increase in the amount of said elastase.

7. The method according to claim 6, further comprising:

analyzing the sample for the amount of said elastase; and confirming that the prediction is correct by determining an increased amount of the elastase.

8. The method according to claim 6, further comprising:

analyzing the sample for said elastase; and diagnosing the patient with platelet thrombosis, wherein the significant increase in said elastase and the significant decrease in said von Willebrand factor-cleaving protease are indicative of platelet thrombosis.

9. The method according to claim 6, further comprising:

analyzing the sample for said elastase; and diagnosing the patient with organ failure, wherein the significant increase in said elastase and the significant decrease in said von Willebrand factor-cleaving protease are indicative of organ failure.

10. The method according to claim 6, further comprising:

analyzing the sample for said von Willebrand factor-cleaving protease; and determining an appropriate treatment option, wherein the significant increase in said elastase and the significant decrease in said von Willebrand factor-cleaving protease are indicative of using an inhibitor of elastase.

* * * * *